United States Patent [19]

Geheb et al.

[11] Patent Number: 5,685,314
[45] Date of Patent: *Nov. 11, 1997

[54] AUXILIARY DOCKING STATION FOR A PATIENT MONITORING SYSTEM

[75] Inventors: Frederick J. Geheb, Danvers; Clifford M. Kelly, Windham; Steven Venditti, Newton, all of Mass.

[73] Assignee: Siemens Medical Systems, Inc., Iselin, N.J.

[*] Notice: The term of this patent shall not extend beyond the expiration date of Pat. No. 5,375,604.

[21] Appl. No.: 414,888

[22] Filed: Mar. 31, 1995

Related U.S. Application Data

[63] Continuation-in-part of Ser. No. 401,332, Mar. 9, 1995, which is a continuation of Ser. No. 252,153, Jun. 1, 1994, abandoned, which is a continuation of Ser. No. 989,410, Dec. 11, 1992, abandoned.

[51] Int. Cl.$^6$ .................................................... A61B 5/0205
[52] U.S. Cl. ................................................................ 128/700
[58] Field of Search ........................................ 128/696, 700; 364/413.06, 413.02

[56] References Cited

U.S. PATENT DOCUMENTS 5,375,604  12/1994  Kelly et al. ........................... 128/671

Primary Examiner—William E. Kamm
Assistant Examiner—Scott Getzow
Attorney, Agent, or Firm—Lawrence C. Edelman

[57] ABSTRACT

A monitor system for acquiring medical data from a plurality of sensors adapted for coupling to a patient located in a given patient monitoring area. The system comprises a portable monitor, a peripheral device, and a docking station. The portable monitor is adapted to be coupled to the plurality of sensors for receiving, processing and displaying patient data signals acquired from the plurality of sensors The peripheral device requires connection to the monitoring system, and comprises, i.e., a strip chart recorder. The docking station is located within the given patient monitoring area and includes at least first and second docking station platforms adapted for being selectively coupled to the portable monitor and the peripheral device respectively, for providing data transfer between the peripheral device and the portable monitor while the portable monitor acquires medical data from the patient.

6 Claims, 4 Drawing Sheets

AUXILIARY DOCKING STATION FOR A PATIENT MONITORING SYSTEM

CROSS-REFERENCE TO RELATED APPLICATIONS

This is a continuation-in-part of application Ser. No. 08/401,332 filed Mar. 9, 1995, pending, which was a continuation of application Ser. No. 08/252,153 filed Jun. 1, 1994, abandoned, which was a continuation of application Ser. No. 07/989,410 filed Dec. 11, 1992, abandoned.

FIELD OF THE INVENTION

The present invention relates to medical systems, and in particular to portable patient monitoring systems for collecting, storing, and displaying medical data.

BACKGROUND OF THE INVENTION

In hospitals and other health care environments, it is often necessary to continuously collect and analyze a variety of medical data from a patient. These data may include electrocardiogram, temperature blood pressure, respiration, pulse and other parameters.

Patient monitoring systems have typically fallen into one or two general categories: multi-function monitoring, recording and displaying systems which process and collect all of the data desired, but are bulky and difficult to transport; and small, portable systems which are easy to transport, but process and collect fewer types of data and have limited storage capability. Initially (e.g., in an ambulance or an emergency room) a patient is connected to a simple, portable monitor to observe a limited number of medical attributes, such as EKG or non-invasive blood pressure. As the patient moves to higher care facilities (e.g., an intensive care unit or operating room it is desirable to augment these simple monitors to observe additional parameters. Generally, this is accomplished by disconnecting the patient from the simple monitor and connecting the patient to a monitoring system having more robust capabilities.

The need for continuity of data collection and display is most pressing in emergency situations. During an emergency, the speed at which a patient is transferred from a bed to an operating room or intensive care unit may substantially impact the patient's chance of survival. It is important to provide the same level of monitoring in transport as at the stationary bedside. It is desirable from a clinical point of view to provide a continuous monitoring capability and data history availability which follows the patient.

Two major considerations in the design of transport monitoring systems are the ease and speed of system reconfiguration. It is undesirable to disconnect from the patient a set of sensors coupled to a fixed location monitoring system, and then attach a new set of sensors coupled to a portable monitor immediately prior to transportation or administration of critical procedures. It is equally undesirable to switch monitoring systems, from a fixed location monitoring system to a portable monitoring system for transport, due to disconnection/reconnect of the individual sensors.

U.S. Pat. No. 5,375,604, titled TRANSPORTABLE MODULAR PATIENT MONITOR, assigned to the same Assignee as the present invention, describes a transportable patient monitoring system of the type including a docking station which both physically and electrically supports a transportable patient monitor.

Although the system described in the '604 patent is a vast improvement over the prior art, further improvement is desirable. That is, typically there are peripheral devices that require connection to the monitoring system, such as a strip chart recorder, a patient ventilator system, etc. Connection of such peripheral devices often leads to a maze of electrical cables traversing the patient monitoring area. Additionally, connection/disconnection of such peripheral devices is not only cumbersome, but also prone to misconnection during emergency and/or rush procedures. Furthermore, such peripheral device are often transported with the patient in order to save the time required for connection/disconnection of such peripheral devices.

It would be desirable to have a patient monitoring system in which patient monitors and peripheral devices can be easily connected and disconnected from one another whenever the monitor is moved from one patient care area to another or the monitoring system is being reconfigured.

It is an object of the present invention to provide a patient monitoring system in which peripheral devices are easily connected/disconnected.

SUMMARY OF THE INVENTION

A monitor system for acquiring medical data from a plurality of sensors adapted for coupling to a patient located in a given patient monitoring area. The system comprises a portable monitor, at least one peripheral device, and a docking station. The portable monitor is adapted to be coupled to the plurality of sensors for receiving, processing and displaying patient data signals acquired from the plurality of sensors. The peripheral device requires connection to the monitoring system, and comprises, i.e., a strip chart recorder. The docking station is located within the given patient monitoring area and includes at least first and second docking station platforms adapted for being selectively coupled to the portable monitor and the peripheral device, respectively, for providing data transfer between the peripheral device and the portable monitor while the portable monitor acquires medical data from the patient.

DETAILED DESCRIPTION OF THE EXEMPLARY EMBODIMENTS

Figure 1:
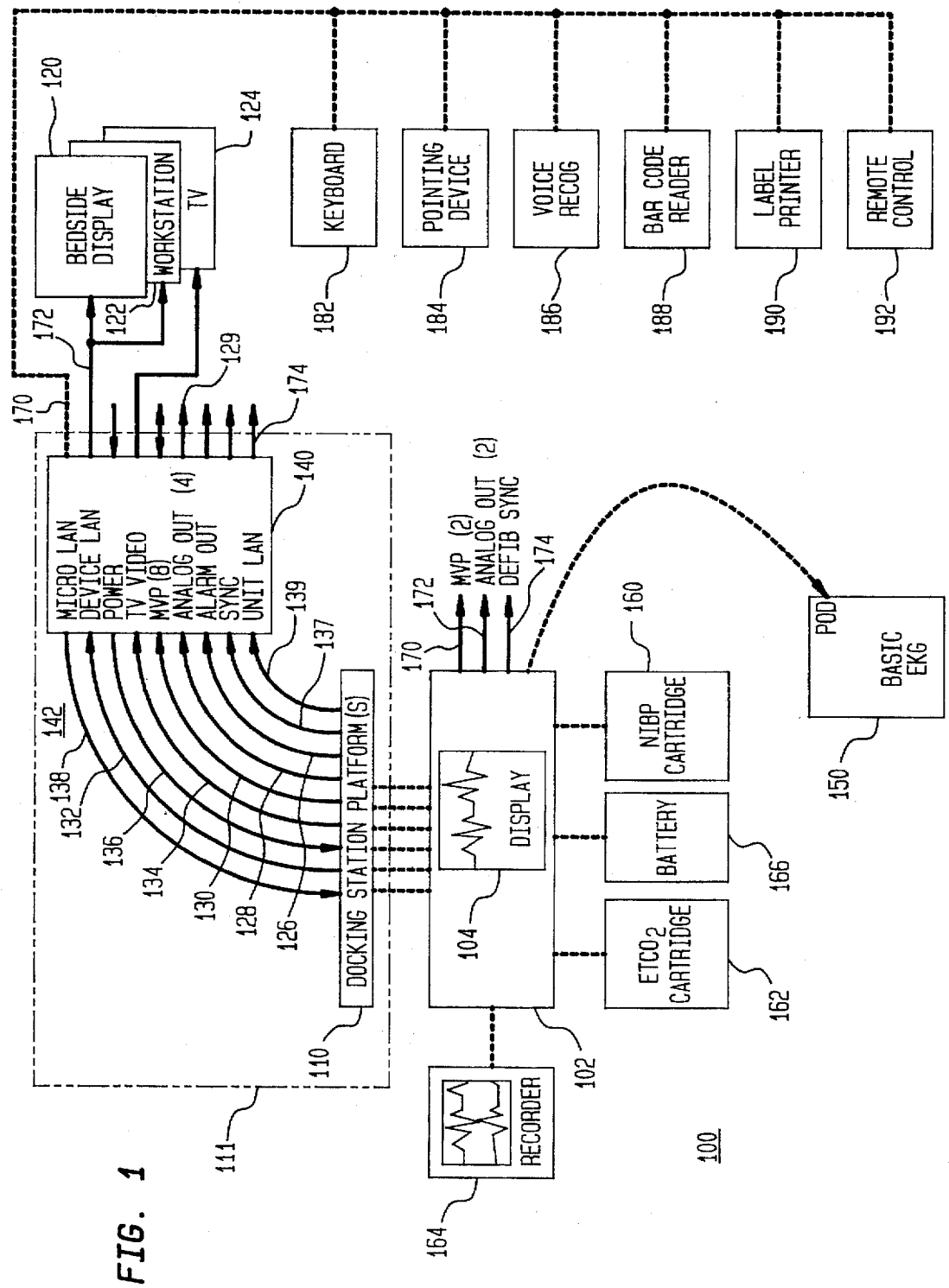
FIG. 1 illustrates in block diagram form a patient monitoring system constructed in accordance with the present invention

An exemplary patient monitoring docking station system 100 including a docking station 111 and docking station platforms 110 in accordance with the present invention is shown in FIG. 1. A portable monitor 102 acquires physiological data signals from a plurality of sensors (not shown), which may include both invasive and non-invasive devices for collecting physiological data from a patient. The portable monitor 102 displays the physiological data, and transmits patient data signals to docking station 111 (It will be understood by one skilled in the art that the term "patient data", as used herein, may refer to the processed information derived from the signals produced by sensors attached to the patient. Thus "patient data" in this sense may include, for example, red, green and blue raster-scan video signals to drive a slave display, or signals to provide status and control information to control peripheral devices). The docking station 111 provides power and communications services to the portable monitor 102 while monitor 102 is mounted on the docking station. The mounting mechanism provides for rapid connection/disconnection of monitor 102 from docking station 111 (both mechanically and electrically) for transport. Preferably, the connection/disconnection is accomplished in a single step, so that the user can easily "pick-up and go" with monitor 102 to transport it to another location in the monitoring system, without handling any individual cables or connectors.

Docking station 111 includes three modular components. In accordance with the principles of the invention, the first two components are monitor and peripheral docking station platforms 110' and 110", respectively. A docking station platform which supports a portable monitor 102 is referred to as a monitor docking station 110' and a docking station platform which supports a peripheral device is referred to as a peripheral docking station 110". Portable monitor 102 may be placed on docking station 110', which may be positioned in the patient area, for example, near the patient's bed or attached to the bedframe. Peripheral docking station 110" provides mechanical support and electrical connections for peripheral equipment such as a strip chart recorder 164 or other such devices.

Note, a plurality of peripheral docking stations 110" could be used to provide a means for these peripheral devices to communicate with local area networks and portable monitors 102 which form a part of patient monitoring system 100.

Peripheral docking station 110" is nearly identical in mechanical form and function to monitor docking station 110'; however, it has a different electrical connector and is keyed in such a way as to prevent portable monitors from being connected to a peripheral docking station platform and vice versa. As used herein, the term portable devices is comprises portable monitors 102, recorders 164 or other devices which can be mounted on a docking station platform 110.

Docking station platforms 110 provide both mechanical support for portable monitor 102 and recorder 164, as well as connections to bedside display 120, a source of operating power 134, and a large format video display 124. Docking Station 111 can also communicate with local area networks (LANs) via couplings 170, 172 and 174, and, via the networks, may provide communications with a computer or an intelligent workstation 122. Docking station 111 provides a simple mechanism to connect portable monitoring devices with several devices and networks without the need to connect individual cables for each device or network. Data and power connectors on the docking station platform 110 and on the cases of the portable devices (102, 164) allow simultaneous physical and electrical couplings to be established.

Figure 2:
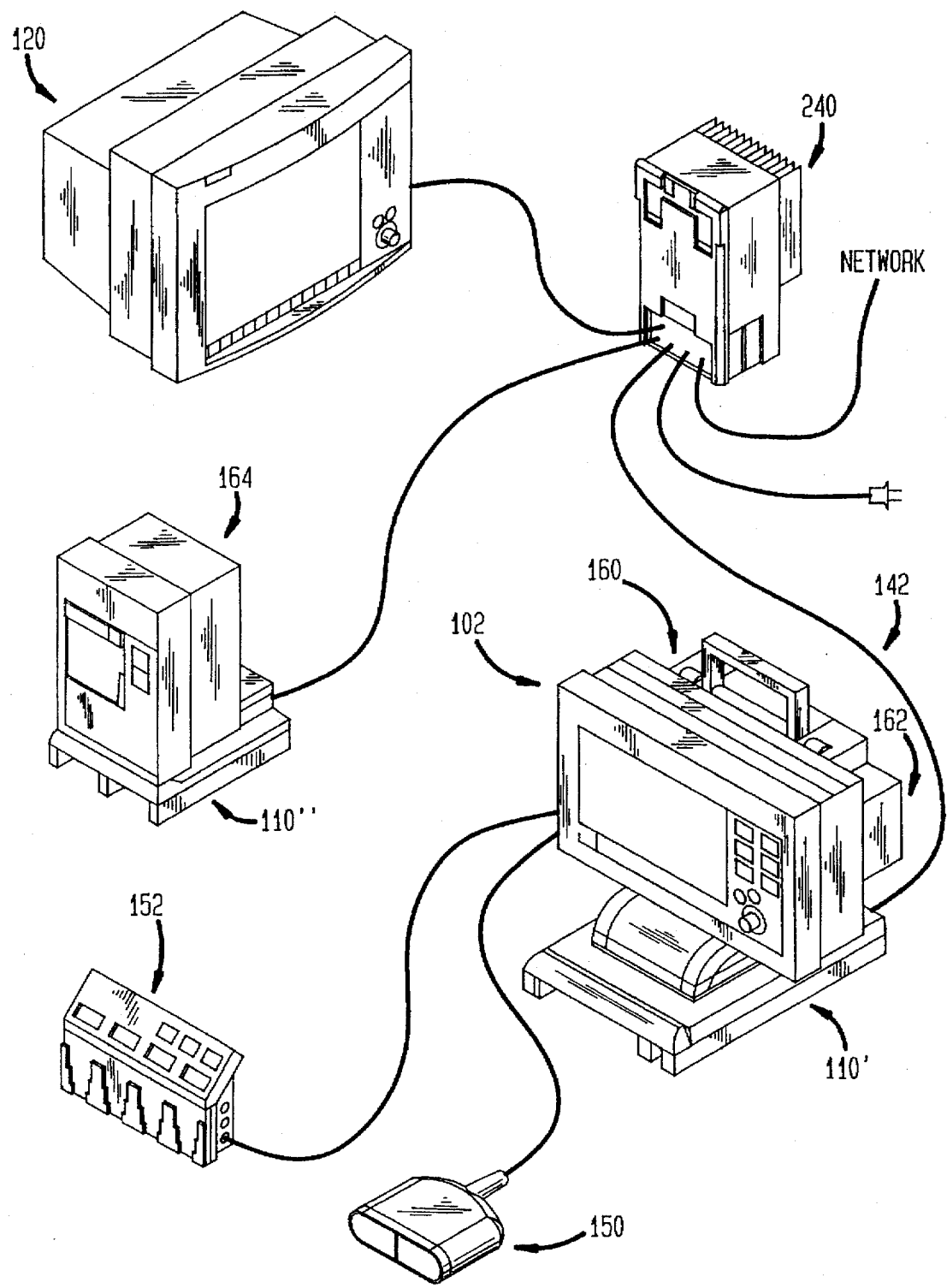
FIG. 2 illustrates an isometric view the use of multiple docking station platforms in accordance with the invention, a patient monitor, a recorder and other peripheral devices shown in FIG. 1.
Figure 4:
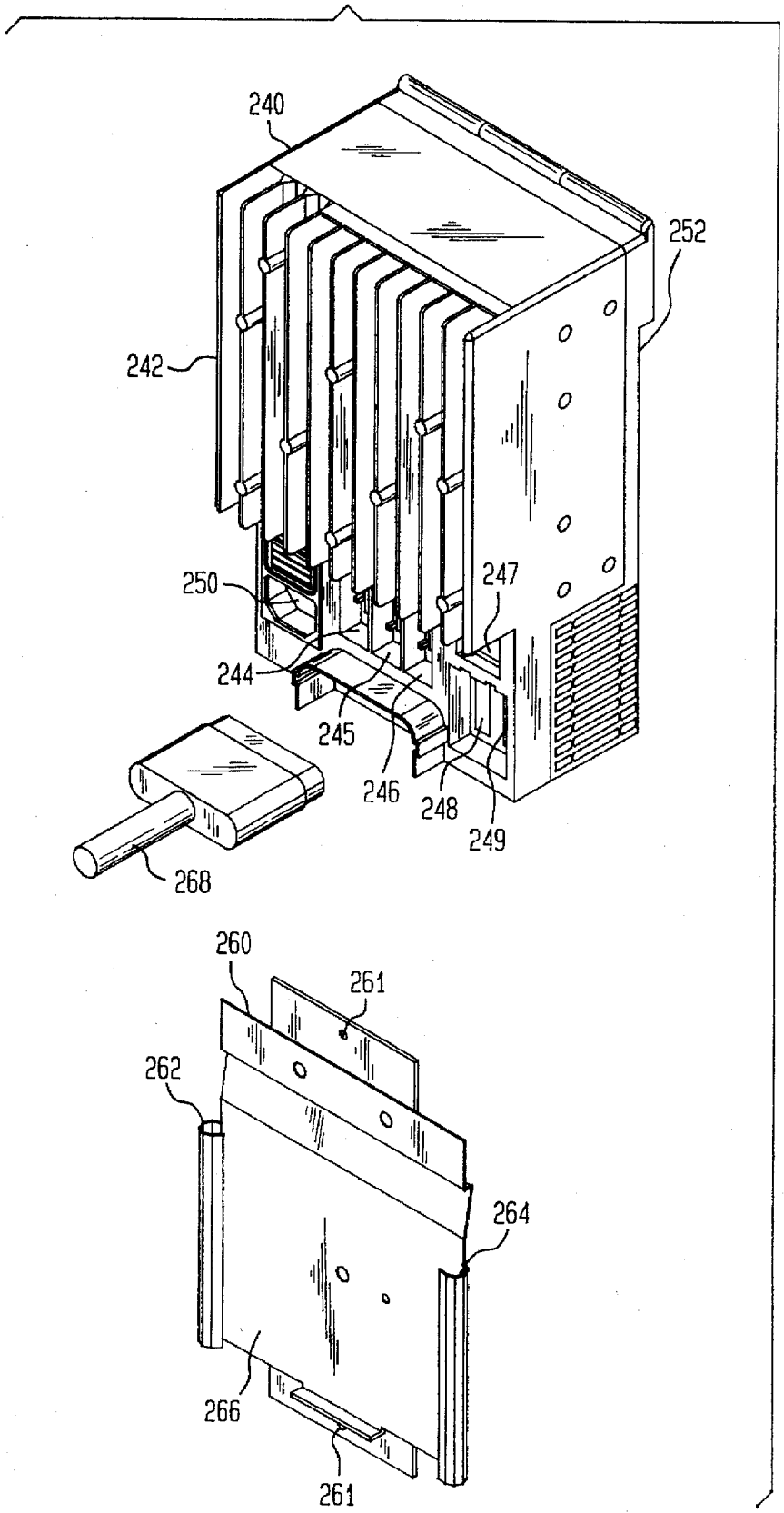
FIG. 4 illustrates an isometric front view of apparatus suitable for use as the wallbox shown in FIG. 2.

The third component of the docking station is a power supply and network box 140 referred to herein as wallbox 140, and in an alternative embodiment shown in FIGS. 2 and 4, as a power supply and network box (PSN) 240. In the FIG. 1 embodiment, wallbox 140 is physically included in docking station 111. In the FIG. 2 (and 4) embodiment, wallbox 140 is physically separate from docking station platforms 110, and is coupled to docking station platforms 110 via connectors 110a and 110h of cable 110m, as shown in FIG. 2. In either embodiment, the functions provided by wallbox 140 and PSN 240 are very similar, and throughout the description this should be kept in mind. Wallbox 140 provides power for operating monitor 102 and for charging a battery pack within (or attached to) monitor 102. Wallbox 140 also provides communications links to networks and devices, both inside and outside of the room in which docking station 111 is located.

Eight multi-vendor ports (MVP) 130 are provided to connect serial devices to the portable monitor and remote stations on the network using a known communications interface, e.g., the RS-232 interface standard.

Portable monitor 102 is a self-contained, standalone monitoring system. Monitor 102 includes all of the processing electronics necessary to process, display and store patient data during transport. In the exemplary embodiment described herein, portable monitor 102 does not include a broad suite of network interfaces; during transport, the exemplary monitor 102 does not have any connections to a central monitoring system or to communications networks. Portable monitor 102 has a rechargeable battery pack for use during transport. Portable monitor is also capable of receiving power from an external power supply. Power may be received from wallbox 140 by way of docking station platform 110, and, in the portable version of wallbox 140, i.e., PSN 240, it can be received using an electrical cable or by direct mounting of PSN 240 on the case of monitor 102.

The bedside display 120 may be a slave unit receiving signal for display from docking station 111. Alternately, bedside display 12 may be an intelligent display unit, complete with a user interface. Alternately, the bedside display may be an intelligent workstation 12 with a VGA display and conventional disk storage.

FIG. 2 shows an isometric view of an exemplary embodiment of the invention, including a docking station platform 110, a PSN 240, and monitor assembly 100 of FIG. 1. The docking station platform 12 is connected to PSN 240 by one or more cables 142. Portable monitor 102 is mounted on docking station platform 110', providing physical support, power, and communications. Monitor 102 acquires physiological data signals from data acquisition pods 150 and 152. Pod 150 provides data from ECG, SpO2 and Temperature sensors. Pod 152 provides data from Invasive Blood Pressure, Cardiac Output and Temperature sensors. A Noninvasive Blood Pressure cartridge 160 and an End tidal CO2 cartridge 162 collect additional patient data. Cartridges 160 and 162 and a battery pack 166 are individually attached to the case of portable monitor 102 for purposes of illustration. The recorder 164 shown connected to the monitor system via mounting on docking station 110". Note: FIG. 2 is illustrative of multiple docking station platforms 110 in a specific patient monitoring area. In a hospital or other health care facility docking station platforms 110' and 110" will be distributed throughout the facility in geographically separate areas, yet they will all be connected to one another for transfer of patient data via wallboxes 140, PSN's 240 and the system communication networks.

Figure 3:
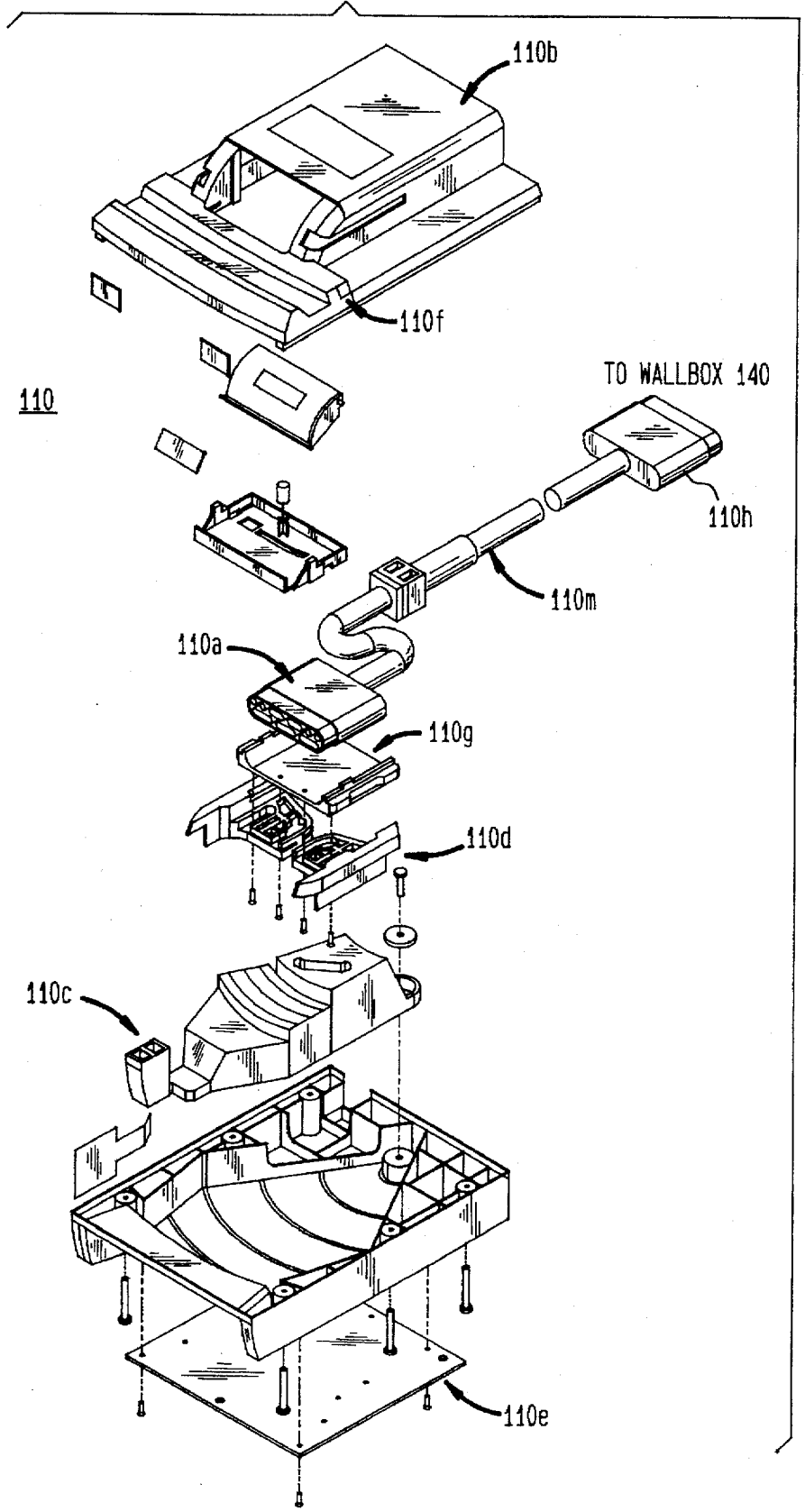
FIG. 3 illustrates an exploded view of one of the docking station platforms shown in FIG. 2.

FIG. 3 shows an exploded view of an exemplary docking station platform 110 to which portable devices may be attached. Cable 110m carries electrical signals from the PSN 240 to the portable device, through the docking station. Cable 268 conveys the signals on conductors 126 through 139 shown in FIG. 1. The connector 110a at the docking station end of cable 110m is attached to a trolley 110g and the connector 110h at the other end of cable 110m is attached to the portable devices.

A docking station top cover 110b not only functions as a protective cover, but also as a guide for mounting the portable devices. Cover 110b provides initial alignment using tapered outer edges and smooth rounded outer surfaces. Once aligned, contours on the top cover funnels the portable device into accurate final alignment using positioning keys 110f, comprising one of more shaped indentation in the surface of top cover 110b. Once positioned, locking rail snaps 110d, flexibly protruding from the left and right sides on top cover 110b, fix the device to the docking station. Docking station electrical connector 110a is then engaged with the corresponding electrical connector in the portable device by moving a lever arm 110d which cams the docking station trolley 110g forward to mate with the corresponding connector in the portable device. The portable device is disengaged by moving lever arm 110c back to the initial position and release is accomplished by moving lever arm 110c an additional amount using the reverse motion of the cam to retract the flexible locking snaps 110d from protruding from the sides of top cover 110b, thereby unlocking the portable device from the portable docking station.

Positioning keys 110f facilitate accurate alignment of the device and the docking station platform 110. In addition, these keys prevent inadvertent placement of a portable monitor on an peripheral docking station 110', or a peripheral device (i.e. recorder) onto a monitor docking station 110".

Many variations of the docking station mechanical configuration are possible. There may be different technologies used to transmit data between portable monitor 102 and docking station 111. Examples of these technologies include infra red and radio frequency transmission techniques. It is understood by one skilled in the art that several such technologies are possible to be used with or as a replacement for cable 110m.

A mounting adaptor 110e may be used to attach the docking station platform 110 in a variety of locations, including but not limited to: an intravenous (IV) pole (not shown), a shelf, a mounting arm or a bed frame. When mounting the docking station platform 110 to a bed or IV pole, both of which are movable, it is desirable to provide a fixed position wallbox 140 for coupling the docking station with power, devices and networks outside of the room in which the docking station is located. A PSN 240 mounted on a wall is suitable for this purpose.

Referring again to FIG. 3, cable 110m provides power to the portable device as well as data communications links from portable device to external devices and networks, when portable devices are on docking station platform 110. Cable 110m may be a conventional connector which interfaces directly to a local area network (LAN). The network may use one of a variety of known LAN protocols, such as carrier sense multiple access with collision detection (CSMA/CD). Additionally, the data may be output to a conventional patient monitoring system bedside display 120 and/or to a customized intelligent workstation 122. Docking station 111 electrically isolate electrical paths connected to the portable monitor 102.

Docking station 111 provides 12 volt DC power to the portable monitor 102 via cable 110m, for operating the device when it is mounted on the docking station platform 110. Portable monitor 102 includes a battery charger and a nickel-cadmium battery 166 (shown in FIG. 1). The battery charger includes connectors and a switch to provide charge to the battery. The docking station 111 transmits a signal to the battery charger to activate the switch, so that the battery charger recharges battery 166 while the portable monitor 102 is mounted on the docking station.

The portable monitor 102 includes alarm processing for the physiological parameters monitored. The portable monitor 102 provides an alarm signal to the docking station 111 if any of these alarm conditions is present. The docking station 111 includes a separate line within cable 110m for receiving alarm signals, if these signals are generated by the portable monitor while it is mounted on the docking station. An alarm output signal is received by docking station platform 110 and transmitted via line 126 to the wallbox 140 for closing relays to activate local alarm devices, such as a light or siren.

Docking station 111 may also receive from portable monitor 102 a synchronization signal which may be used to trigger a defibrillator. This signal may then output from the PSN 240.

FIG. 4 shows a power supply network box 240. PSN 240 couples the docking station platform 110 to communications links which may include a plurality of local area networks (LANs) or serial or parallel-bit data links. The PSN 240 includes buffer amplifiers to condition the docking station output signals for transmission over these LANs. In the secondary exemplary embodiment, the PSN 240 includes a network interface card (not shown) which provides two way communication between the portable device and other equipment connected to the LAN 174. This LAN 174 connects portable devices and bedside display 120 with remote stations for transferring patient data. The remote stations may be patient monitoring systems or computers. This LAN 174 is configured to produce message delays of less than 2 seconds It is understood by one skilled in the art that a several LAN protocol may be used for LAN 174.

In the exemplary embodiment, PSN 240 provides a direct video connection to a bedside display 120 using a protocol such as the Electronics Industries Association's RS-232-C Interface Standard. When the portable monitor 102 is on the docking station platform 110, monitor 102 drives bedside display 120, using the RS-232-C link. Alternatively, PSN 240 may include a second conventional interface cable (not shown) for interfacing a second LAN 172 (referred to as the Device LAN), which may, for example, be a 10 Mbit/sec. CSMA/CD LAN, to the PSN 240. The Device LAN is used within a patient's room or operating room, or to distribute patient data via a central station. The Device LAN provides the main communications path to transfer patient data from the portable monitor 102 to a bedside display 120 within the same room in near real-time. This LAN is configured to maintain short delays and to allow a nominal 200 msec. response time between devices.

PSN 240 includes a third interface card (not shown) and a separate connection 138 which provides a coupling to an additional LAN for connecting input and output devices. This additional LAN may use protocol such as High Level Datalink Control (HDLC) with device polling, for predictable response time. This additional LAN is referred to as the Micro LAN 170. The Micro LAN is used to connect input and output devices to the portable monitor 102 by way of the docking station 111. These devices (shown in FIG. 1) may include keyboards 182, pointing devices 184, voice recognition 186 device, a bar code reader 188, a label printer 190, and a remote control 192. The remote control 192 may be either wired or infrared (IR). The wire remote control may be more desirable in an operating room (OR) environment, because the OR lights may distort IR control signals.

Although in the exemplary embodiments three distinct LANs and used for connecting the docking station to remote stations, to local stations (i.e., those within the same room) and to I/O devices, it is understood by those skilled in the field of data communications that a variety of network configurations may be used to achieve a desired level of performance and reliability for these different types of traffic. In addition, the network configuration may be tailored to protect patients by isolating a device or class of devices on a separate LAN to prevent accidental or unauthorized use. Smaller installations may implement a single local area network within a site to accommodate all of the patient monitoring traffic.

PSN 240 (and wall box 140) includes a de-multiplexer and a D/A converter (not specifically shown) which receives digital data from portable monitor 102 and generates a plurality of analog waveform signals from the digital data. The analog signals are sent to port 129. Four analog output ports provide waveform data for transmission to external devices (e.g., displays, recorders). Thus, existing analog equipment may be connected to the portable monitor (which provides patient data in digital form in the exemplary embodiment) in order to display data collected by the monitor. By de-multiplexing inside the PSN 240 (as opposed to within the portable monitor 102 or the docking station platform 110), the electrical couplings between monitor 102 and docking station platform 110, and between docking station platform 110 and PSN 240 are simplified.

PSN box 240 detachably mounts to the wall, bed or some other support on a bracket 260. As shown in FIG. 4, bracket 260 may be permanently attached to a wall or other permanent surface, using conventional fasteners driven through mounting holes 261.

In the exemplary embodiment, a plate (not specifically shown on the back of PSN box 240 slides down into a channel 266 formed between grooves 262 and 264 of a bracket 260. Bracket 260 may be permanently attached to a wall or other permanent surface, using conventional fasteners driven through mounting holes 261. PSN box 24p includes a plurality of connectors 244, 245, 246, 247, 248, 249 and 250 for receiving respective cables (not shown). The cables couple the PSN box 240 to networks and to power, as described above with reference to PSN 240 as shown in FIG. 3. Connector 250 receives AC power from the room. Connectors 244 and 245 provide general purpose serial ports. Connector 246 provides serial and video connection to the bedside display 120. Connector 247 provides connection to the LAN 174. Connectors 248 and 249 provide connectors to peripheral docking stations 111. PSN box 240 also includes an enclosed chimney heat sink 242.

As shown in the forenoted U.S. Pat. No. 5,375,604, PSN 240 can also be attached to monitor 102 in a "semi-permanent" manner. When PSN 240 is attached directly to monitor 102, the docking station platform 110 is not used.

The PSN Box 240 shown in FIG. 4 is just one example of the mechanical and electrical configurations that are possible for PSN 240 Other configurations may include a version that mounts directly to portable monitor 102 or a version with fewer or more circuit boards and connectors. In the configuration shown in FIG. 4, PSN box 240 takes over part of the functionality provided by the docking station 111 (i.e., the functionality of wallbox 140).

Although the exemplary PSN 240 shown in FIG. 4 does not have as many ports as wallbox 140 shown in FIG. 1, it is understood by one skilled in the art that a PSN box may be configured with the same number and types of ports as wallbox 140. Internally, PSN may include the same configuration of network interface cards and electronics as wallbox 140. It is understood by one skilled in the art that PSN 240 may be constructed with additional interfaces as desired or the suite of interfaces may be reduced in scope for use in smaller installations, such as the exemplary PSN 240.

The primary difference between wallbox 140 and PSN box 240 is the mechanical packaging. In the configuration shown in FIG. 4, PSN box 240 is a functionally limited version of wallbox 140.

It is understood by one skilled in the art that many variations of the embodiments described herein are contemplated. While the invention has been described in terms of exemplary embodiments, it is contemplated that it may be practiced as outlined above with modifications within the spirit and scope of the appended claims. For example, although only one peripheral docking station platform 110" is shown in the patient area in FIG. 2, clearly, a plurality of such peripheral docking station platforms 110" could be used in a given area, depending upon the number of peripheral devices one desires to connect to the monitoring system.

We claim:

1. A monitor system for acquiring patient data from a plurality of sensors adapted for coupling to a patient located in a given patient monitoring area, the system comprising:

a portable monitor adapted to be coupled to the plurality of sensors for receiving, processing and displaying patient data signals acquired from the plurality of sensors;

a peripheral device for at least one of transmitting and receiving patient data signals;

a communication device located within said patient monitoring area for providing data transfer for patient data signals coupled thereto; and at least first and second docking stations located within said given patient monitoring area and adapted for being selectively coupled to said portable monitor and said peripheral device, respectively, each of said first and second docking stations also being coupled to said communication device for providing patient data signal transfer between said peripheral device and said portable monitor while said portable monitor acquires patient data from said patient and said portable monitor and peripheral device are coupled to said first and second docking stations, respectively.

2. The monitor system of claim 1, wherein said second docking station provides bi-directional data transfer between said peripheral device and said portable monitor, via said communication device, while said portable monitor acquires patient data from said patient.

3. The monitor system of claim 1, wherein said first and second docking stations comprises first and second types of support platforms, respectively, adapted for electrical and mechanical connection to said portable monitor and said peripheral device, respectively.

4. The monitor system of claim 3, wherein said first and second types of support platforms each include;

a guide mechanism for guiding an electrical connector in a respective one of said peripheral device and said portable monitor into mechanical alignment with an electrical connector in said support platform; and a latch mechanism for causing selective electrical engagement of the electrical connectors in said peripheral device and portable monitor, as well as mechanical fixation of said portable monitor and peripheral device to said support platform.

5. The monitor system of claim 1, wherein said communication device is coupled to a data communication network providing for transfer of patient data signals outside of said given patient monitoring area.

6. The monitor system of claim 3, wherein said communication device includes a source of power, for providing operating power to said portable monitor and said peripheral device, via said first and second types of support platforms, respectively.

* * * * *